(12) United States Patent
Hardert

(10) Patent No.: US 8,323,307 B2
(45) Date of Patent: Dec. 4, 2012

(54) BALLOON CATHETER WITH DILATING ELEMENTS

(75) Inventor: Michael W. Hardert, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 895 days.

(21) Appl. No.: 12/029,700

(22) Filed: Feb. 12, 2008

(65) Prior Publication Data
US 2008/0200944 A1    Aug. 21, 2008

Related U.S. Application Data

(60) Provisional application No. 60/901,522, filed on Feb. 13, 2007.

(51) Int. Cl.
*A61M 29/00* (2006.01)

(52) U.S. Cl. .................................................. 606/194

(58) Field of Classification Search .............. 606/159, 606/191–199, 170, 180; 623/1.11, 1.12; 604/96.01, 103.08, 103.09
See application file for complete search history.

(56) References Cited

U.S. PATENT DOCUMENTS

| | | |
|---|---|---|
| 4,729,763 A | 3/1988 | Henrie |
| 4,886,061 A | 12/1989 | Fischell et al. |
| 4,886,062 A * | 12/1989 | Wiktor ........................ 606/194 |
| 4,898,575 A | 2/1990 | Fischell et al. |
| 4,983,167 A | 1/1991 | Sahota |
| 5,019,042 A | 5/1991 | Sahota |
| 5,030,201 A | 7/1991 | Palestrant |
| 5,047,040 A | 9/1991 | Simpson et al. |
| 5,057,120 A | 10/1991 | Farcot |
| 5,078,723 A | 1/1992 | Dance et al. |
| 5,080,660 A | 1/1992 | Buelna |
| 5,090,958 A | 2/1992 | Sahota |
| 5,112,305 A | 5/1992 | Barath et al. |
| 5,147,377 A | 9/1992 | Sahota |
| 5,160,321 A | 11/1992 | Sahota |
| 5,181,920 A | 1/1993 | Mueller |
| 5,192,291 A | 3/1993 | Pannek, Jr. |
| 5,196,024 A | 3/1993 | Barath |

(Continued)

FOREIGN PATENT DOCUMENTS

EP    0 117 519    2/1984

(Continued)

OTHER PUBLICATIONS

Delphion printout—English title and abstract for EPA 0 117 519—1 page.

*Primary Examiner* — Gary Jackson
*Assistant Examiner* — Lindsey Bachman
(74) *Attorney, Agent, or Firm* — Brinks Hofer Gilson & Lione

(57) ABSTRACT

A balloon catheter is provided that may be used to dilate hardened regions of a stenosis. The balloon catheter is provided with dilation elements that extend along a surface of a balloon. The dilation elements may comprise a coil and dilation wire. The coil and wire may be configured in various ways such that inflation of the balloon creates a concentration of forces along the dilating wires which are thereafter transmitted to stenosed regions of a vessel wall. The force exerted by the dilation elements against the stenosed region is sufficient to fracture plaque from the vessel wall.

11 Claims, 7 Drawing Sheets

U.S. PATENT DOCUMENTS

| | | | |
|---|---|---|---|
| 5,209,749 A | 5/1993 | Buelna | |
| 5,224,945 A | 7/1993 | Pannek, Jr. | |
| 5,224,949 A | 7/1993 | Gomeinger et al. | |
| 5,320,605 A | 6/1994 | Sahota | |
| 5,320,634 A * | 6/1994 | Vigil et al. | 606/159 |
| 5,336,178 A | 8/1994 | Kaplin et al. | |
| 5,372,601 A | 12/1994 | Lary | |
| 5,395,332 A | 3/1995 | Ressemann | |
| 5,409,454 A | 4/1995 | Fischell et al. | |
| 5,411,478 A | 5/1995 | Stillabowerer et al. | |
| 5,431,673 A | 7/1995 | Summers | |
| 5,441,510 A | 8/1995 | Simpson | |
| 5,505,725 A | 4/1996 | Samson | |
| 5,556,408 A | 9/1996 | Farhat | |
| 5,571,087 A | 11/1996 | Ressemann | |
| 5,575,771 A | 11/1996 | Walinsky | |
| 5,601,582 A | 2/1997 | Shelton et al. | |
| 5,616,149 A | 4/1997 | Barath | |
| 5,624,704 A | 4/1997 | Darouiche et al. | |
| 5,628,746 A | 5/1997 | Clayman | |
| 5,690,642 A | 11/1997 | Osborne et al. | |
| 5,722,949 A | 3/1998 | Sanese | |
| 5,728,129 A | 3/1998 | Summers | |
| 5,779,698 A | 7/1998 | Clayman et al. | |
| 5,792,158 A | 8/1998 | Lary | |
| 5,797,935 A | 8/1998 | Barath | |
| 5,814,061 A | 9/1998 | Osborne et al. | |
| 5,904,679 A * | 5/1999 | Clayman | 606/39 |
| 5,910,144 A | 6/1999 | Hayashi | |
| 5,921,958 A * | 7/1999 | Ressemann et al. | 604/96.01 |
| 6,033,380 A | 3/2000 | Butaric et al. | |
| 6,036,689 A | 3/2000 | Tu et al. | |
| 6,036,708 A | 3/2000 | Sciver | |
| 6,071,285 A | 6/2000 | Lashinski et al. | |
| 6,123,718 A | 9/2000 | Tu et al. | |
| 6,165,187 A | 12/2000 | Reger | |
| 6,231,572 B1 | 5/2001 | Hart et al. | |
| 6,245,040 B1 | 6/2001 | Inderbitzen et al. | |
| 6,280,464 B1 | 8/2001 | Hauashi | |
| 6,283,947 B1 | 9/2001 | Mirzaee | |
| 6,306,151 B1 | 10/2001 | Lary | |
| 6,355,013 B1 | 3/2002 | Van Muiden | |
| 6,371,961 B1 | 4/2002 | Osborne et al. | |
| 6,500,186 B2 | 12/2002 | Lafontaine et al. | |
| 6,517,548 B2 * | 2/2003 | Lorentzen Cornelius et al. | 606/108 |
| 6,632,231 B2 | 10/2003 | Radisch | |
| 6,746,463 B1 | 6/2004 | Schwartz | |
| 6,808,531 B2 | 10/2004 | Lafontaine et al. | |
| 6,855,124 B1 | 2/2005 | Gonzalez | |
| 2003/0028212 A1 | 2/2003 | Saab | |
| 2003/0114877 A1 | 6/2003 | Gellman | |
| 2003/0130683 A1 * | 7/2003 | Andreas et al. | 606/200 |
| 2004/0073297 A1 | 4/2004 | Rohde et al. | |
| 2004/0122465 A1 * | 6/2004 | McMurtry et al. | 606/194 |
| 2004/0143287 A1 | 7/2004 | Konstantino et al. | |
| 2004/0193196 A1 | 9/2004 | Appling et al. | |
| 2004/0199191 A1 | 10/2004 | Schwartz | |
| 2005/0021070 A1 | 1/2005 | Feld et al. | |
| 2005/0021071 A1 | 1/2005 | Konstantino et al. | |
| 2005/0240212 A1 * | 10/2005 | McAuley et al. | 606/194 |
| 2005/0288629 A1 | 12/2005 | Kunis | |
| 2006/0111736 A1 | 5/2006 | Kelley | |
| 2006/0173487 A1 | 8/2006 | Uflacker et al. | |
| 2007/0073329 A1 | 3/2007 | Hardert | |
| 2007/0106215 A1 | 5/2007 | Olsen | |

FOREIGN PATENT DOCUMENTS

| | | |
|---|---|---|
| WO | WO 2004/066852 | 8/2004 |

* cited by examiner

BALLOON CATHETER WITH DILATING ELEMENTS

RELATED APPLICATIONS

This application claims the benefit of priority from U.S. Provisional Application No. 60/901,522 filed Feb. 13, 2007, which is incorporated herein by reference.

BACKGROUND

The present invention relates generally to medical devices and more particularly to balloon catheters used to dilate narrowed portions of a lumen.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. This has lead to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed coronary arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters. Although the inventions described below may be useful in treating hardened regions of stenosis, the claimed inventions may also solve other problems as well.

SUMMARY

A balloon catheter is provided that may be used to dilate hardened regions of a stenosis. The balloon catheter is provided with dilation elements that extend along a surface of a balloon. The dilation elements comprise a coil and dilation wire. The coil and the dilation wire may be configured with each other in various ways. As the balloon is expanded, the balloon exerts a concentration of forces against the dilation wire. The concentration of forces may allow the dilation elements to transmit a concentrated force at a stenosed region. The concentrated force exerted by the dilation elements against the stenosed region is sufficient to fracture plaque from the vessel wall. Additional details and advantages are described below in the detailed description.

The invention may include any of the following aspects in various combinations and may also include any other aspect described below in the written description or in the attached drawings.

A balloon catheter for dilation of a vessel wall, comprising: a shaft having a distal end and a proximal end, a balloon mounted on the distal end of the shaft, the balloon having a distal portion, a proximal portion, wherein at least a length of an outer surface of the balloon comprises a working diameter adapted to dilate the vessel wall, the shaft having an inflation lumen extending therethrough in fluid communication with an interior region of the balloon, the balloon thereby being expandable between a deflated state and an inflated state, and a dilation element comprising a proximal coil, a distal coil, and a dilation wire, the dilation wire having a proximal end, a distal end, and a middle portion, the middle portion of the dilation wire extending along the working diameter on an outer surface of the balloon, the proximal end of the dilation wire affixed to the proximal coil, wherein the proximal coil proximally extends from the working diameter of the balloon to the shaft, the distal end of the dilation wire affixed to the distal coil, wherein the distal coil distally extends from the working diameter of the balloon to the shaft, the proximal and the distal coils being affixed to the shaft.

The balloon catheter, wherein the number of dilation elements is three.

The balloon catheter, wherein each of the three dilation elements are circumferentially spaced about the outer surface of the balloon.

The balloon catheter, wherein the proximal end of the dilation wire is affixed to the proximal coil at a location different from the location where the proximal coil is affixed to the shaft.

The balloon catheter, wherein the distal end of the dilation wire is affixed to the distal coil at a location different from the location where the distal coil is affixed to the shaft.

The balloon catheter, wherein the middle portion of the dilation wire is rigid.

The balloon catheter, wherein the distal end of the dilation wire is affixed to the distal coil at a first location and the distal coil is affixed to the shaft at a second location, the distance between the first location and the second location defining a region of stretchability of the distal coil.

The balloon catheter, wherein the proximal end of the dilation wire is affixed to the proximal coil at a third location and the distal coil is affixed to the shaft at a fourth location, the distance between the third location and the fourth location defining a region of stretchability of the proximal coil.

The balloon catheter, wherein the proximal end of the dilation wire and the distal end of the dilation wire are ground.

The balloon catheter, wherein the proximal end of the dilation wire and the distal end of the dilation wire are tapered.

The balloon catheter, the balloon catheter comprising a plurality of dilating elements circumferentially disposed relative to each other, each of the plurality of dilating elements comprising a dilation wire, and wherein the balloon has a plurality of creases about an outer surface of the balloon, the plurality of creases forming flaps when the balloon is in the deflated state, the flaps folding around each of the plurality of dilation wires, the flaps being in substantial parallel alignment with the longitudinal axis of the balloon.

The balloon catheter, wherein the proximal end of the dilation wire is affixed to the proximal coil and the distal end of the dilation wire is affixed to the distal coil.

The balloon catheter, wherein the dilation wire is circular-shaped.

The balloon catheter, wherein the dilation wire is non-circular shaped.

A balloon catheter for dilation of a vessel wall, comprising: a shaft having a distal end and a proximal end, a balloon mounted on the distal end of the shaft, the balloon having a distal portion, a proximal portion, wherein at least a length of an outer surface of the balloon comprises a working diameter adapted to dilate the vessel wall, the shaft having an inflation lumen extending therethrough in fluid communication with an interior region of the balloon, the balloon thereby being expandable between a deflated state and an inflated state, and a dilation element comprising a coil and a dilation wire, a dilation element comprising a coil and a dilation wire, the dilation wire having a proximal end and a distal end, one of the proximal and the distal ends of the dilation wire affixed to the coil, the coil extending in a first direction from at least the working diameter of the balloon to the shaft.

The balloon catheter, wherein the other one of the proximal and the distal ends of the dilation wire is affixed to the shaft The balloon catheter, wherein the dilation wire extends from the inner surface of the coil to the working diameter along an outer surface of the balloon.

The balloon catheter, the coil being affixed to the shaft and heat shrink tubing being disposed over the shaft.

The balloon catheter, wherein the coil continuously extends from the proximal portion to the distal portion of the balloon, the dilation wire affixed to the coil at the working diameter of the balloon.

The balloon catheter, wherein the proximal end and the distal end of the dilation wire are affixed to the coil.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
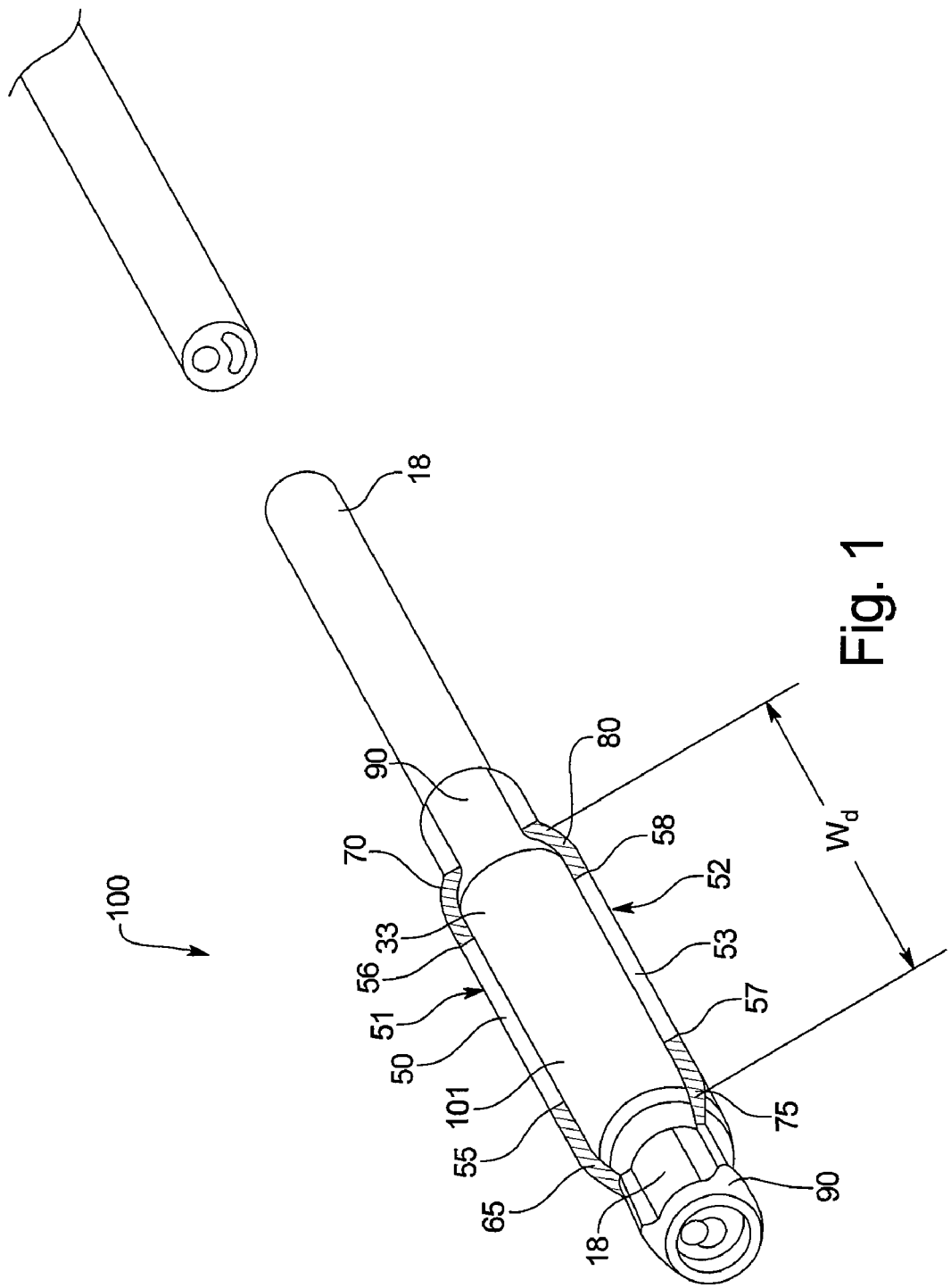
FIG. 1 is a side elevational view of a balloon catheter with a deflated balloon and dilation elements extending along the balloon.

FIG. 1 illustrates a balloon catheter 100 with a balloon 101 comprising a preferred design configuration of dilation elements 51 and 52 disposed along an outer surface of the balloon 101. The balloon 101 is shown in its deflated state. As will be discussed later with respect to FIG. 7, the dilation elements 51 and 52 may be wrapped into the folds of the balloon 101 to prevent the dilation elements 51 and 52 from inadvertently moving. For purposes of clarity, however, FIG. 1 does not show such a pleated configuration to enable illustration of the connection of the dilation elements 51 and 52 to the balloon 101 and shaft 18.

As shown in FIG. 1, the outer surface of the balloon 101 has a working diameter 33 that extends along part of the length of the balloon 101. The length of the working diameter 33, $W_d$, may be defined as the distance between the balloon proximal end, where the tapered proximal portion meets the working diameter 33, and the balloon distal end, where the tapered distal portion meets the working diameter 33. As shown in FIG. 1, the working diameter 33 of the balloon 101 may be connected to the shaft 18 with the tapered proximal portion and the tapered distal portion of the balloon 101. Typically, the working diameter 33 of the balloon 101 is a portion that inflates to a generally uniform circumference in order to evenly dilate a section of a lumen. However, the working diameter 33 does not necessarily need to have a uniform circumference.

Dilation element 51 includes a wire 50, proximal coil 70, and distal coil 65. The wire 50 extends between joints 55 and 56 along the working diameter 33 of the balloon 101. FIG. 1 shows that each of the ends of the wire 50 attaches to a coil. Joint 55 represents the location where the distal end of the wire 50 affixes to distal coil 65, and joint 56 represents the location where the proximal end of the wire 50 affixes to proximal coil 70. Joints 55 and 56 may be any type of joint known to one of ordinary skill in the art, including a tack weld, adhesive joint, or solder joint. Distal coil 65 extends from the working diameter 33 at joint 55 and continues to extend along tapered distal portion of the balloon 101. Distal coil 65 terminates at shaft 18. Distal coil 65 may attach to shaft 18 by an adhesive, such as glue. As FIG. 1 shows, heat shrink tubing 90 may be disposed over the distal coil 65 and extend circumferentially around the catheter shaft 18. The heat shrink tubing 90 may provide a smooth transition from the distal coil 65 to the shaft 18. Proximal coil 70 extends from the working diameter 33 at joint 56 and continues to proximally extend along tapered proximal portion of the balloon 101. The proximal coil 70 terminates at shaft 18 and may attach to shaft 18 by an adhesive, such as glue. Heat shrink tubing 90 may be disposed over the proximal coil 70 and extend circumferentially around the catheter shaft 18. The extension of a portion of the distal and proximal coils 65 and 70 along the working diameter 33 of the balloon 101 enables the coils 65 and 70 to stretch when the balloon 101 is inflated. This coil stretching feature enables the wire 50, which extends along at least a portion of the working diameter 33 of the balloon 101, to dilate a stenosed region without being severed from the surface of the balloon 101. The wire 50 remains rigid as the coils 65, 70 stretch during inflation of the balloon 101. Because the wire 50 remains rigid, it may transfer its force exerted by the inflated balloon 101 to a stenosed vessel wall.

Dilation element 52 includes a wire 53, proximal coil 80, and distal coil 75. Dilation element 52 is configured similar to dilation element 51. The wire 53 extends between joints 57 and 58 along at least a portion of the working diameter 33 of the balloon 101. FIG. 1 shows that each of the ends of the wire 53 attaches to a coil. Joint 57 represents the location where the wire 53 affixes to the distal coil 75, and joint 58 represents the location where the wire 53 affixes to the proximal coil 80. Joints 57 and 58 may be any type of joint known to one of ordinary skill in the art, including a tack weld or solder joint. Distal coil 75 extends from the working diameter 33 at joint 75 and continues to extend along the tapered distal portion of the balloon 101. Distal coil 75 terminates at shaft 18. Distal coil 75 may attach to shaft 18 by an adhesive, such as glue. As FIG. 1 shows, heat shrink tubing 90 may be disposed over the distal coil 75 and extend circumferentially around the catheter shaft 18 to provide a smooth transition from the distal coil 75 to the shaft 18. Proximal coil 80 extends from the working diameter 33 at joint 58 and continues to proximally extend along tapered proximal portion of the balloon 101. The proximal coil 80 terminates at shaft 18 and may attach to the shaft 18 by an adhesive, such as glue. Heat shrink tubing 90 may be disposed over the proximal coil 80 and extend circumferentially around the catheter shaft 18. The extension of a portion of the proximal and distal coils 80 and 75 along the working diameter 33 enables the coils 80 and 75 to stretch when the balloon 101 is inflated. This stretching of the coils 80, 75 enables the wire 53 to dilate a stenosed region without being severed from the surface of the balloon 101. The wire 53 remains rigid as the coils 80, 75 stretch during inflation of the balloon 101. Because the wire 53 remains rigid, it may transfer its force exerted by the inflated balloon 100 to the stenosed vessel wall.

FIG. 1 shows that dilation element 52 is spaced about 120° from dilation element 51. Although not visible on FIG. 1, a third dilation element (shown in FIGS. 3 and 4) may be spaced about 120° from dilation elements 51 and 52. The bumps or ridges along the distal end of the shaft 18 represent the profile that the distal coil 65 creates underneath the shrink tubing 90, which will be explained in greater detail below.

Figure 2:
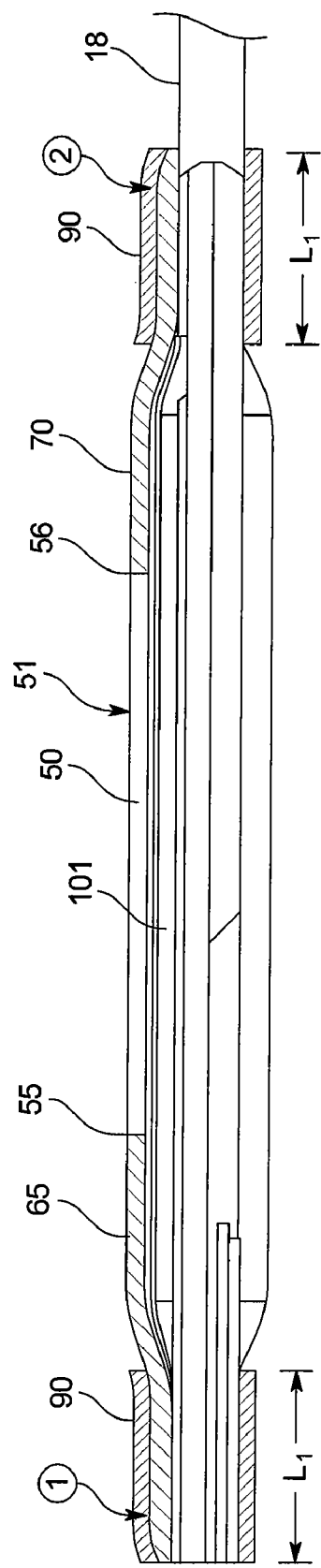
FIG. 2 shows a longitudinal cross-sectional view of the balloon catheter of FIG. 1 cut through dilation element 51.

FIG. 2 shows a longitudinal cross-sectional view of the balloon catheter 100 of FIG. 1 cut through dilation element 51. The cross-sectional view shows in greater detail the connection of dilation element 51 along the surface of the balloon 101. As FIG. 2 shows, each end of the wire 50 is sufficiently tapered to fit into the distal and proximal coils 65 and 70. Although FIG. 2 shows that the wire 50 affixes inside of the coils 65 and 70, the wire 50 may be affixed to the outer surface of the coils 65 and 70. Numerous ways for attaching the wire 50 to the coils 65 and 70 are contemplated. The darkened regions at joints 55 and 56 represent each end of the wire 50 tapering into respective distal and proximal coils 65 and 70. Distal coil 65 extends distally from the working diameter 33 to the shaft 18. The distal coil 65 terminates at the location designated "1." Similarly, proximal coil 70 extends proximally from the working diameter 33 to the shaft 18. The proximal coil 70 terminates at the location designated "2." The tapered regions beyond locations "1" and "2" indicate heat shrink tubing 90 without coils disposed therebelow. Heat shrink tubing 90 extends about the circumference of the shaft 18 at both ends of the balloon 101. The heat shrink tubing 90 adjacent to the distal end of the balloon 101 extends a length L1, and the heat shrink tubing 90 adjacent to the proximal end of the balloon 101 extends a length L2. The lengths L1 and L2 may be dependent upon numerous factors, including the length that proximal coil 70 and distal coil 65 extend along the shaft 18. L1 and L2 generally extend slightly beyond respective locations "1" and "2" in order to create a smooth transition from the coils 65 and 70 to the shaft 18. Although FIGS. 1 and 2 preferably have heat shrink tubing 90, the balloon catheter 100 does not necessarily require the heat shrink tubing 90 for purposes of the embodiments described herein. In the example shown in FIG. 2, the length of the proximal coil 70 and the length of the distal coil 65 along the shaft 18 may be sufficient to provide a predetermined amount of stretchability.

Figure 3:
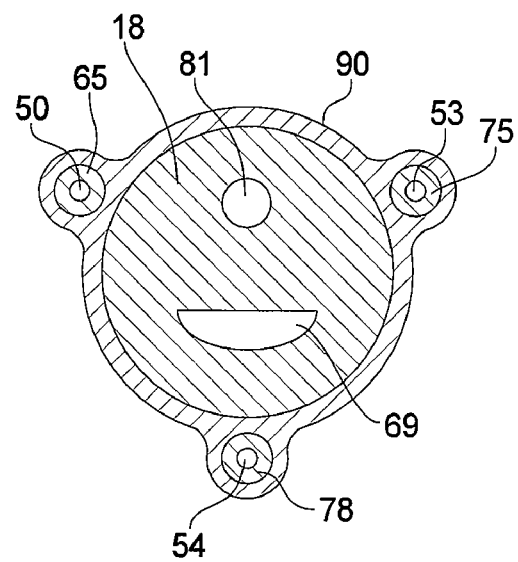
FIG. 3 is a cross-sectional end view of the balloon catheter along the shaft at the proximal end of the balloon of FIG. 1.

FIG. 3 is a cross-sectional end view of the balloon catheter 100 along the shaft 18 at the distal end of the balloon 101 of FIG. 1. Dilation wire 50 is shown disposed within distal coil 65. Similarly, dilation wire 53 is shown disposed within distal coil 75. A third dilation wire 54 (not shown in FIG. 1) is shown disposed within its distal coil 78. The dilation wires 50, 53, 54 may be attached to the inner surface of their respective distal coils 65, 75, 78 at one or more locations. The dilation wires 50, 53, 54 are shown spaced 120° apart from each other. Other angular separations of the dilation wires 50, 53, 54 are contemplated. Additionally, less than three or more than three dilation wires may be used.

FIG. 3 shows the distal coils 65, 75, 78 bonded to a surface of the shaft 18. Heat shrink tubing 90 may be disposed over the coils 55, 65. The heat shrink tubing 90 may be a thin plastic sleeve which may be fitted over at least a portion of the shaft 18 and distal coils 65, 75, 78. When initially placed over the shaft 18 and distal coils 65, 75, 78, the heat shrink tubing 90 has a larger outer diameter. Upon heating the shrink tubing 90, the tubing 90 reduces in diameter to provide a smooth outer surface from the distal coils 65, 75, 78 to the balloon 101. The smooth outer surface facilitates placement and removal of the balloon catheter 101 from a vessel. A cross-sectional end view of the balloon catheter 100 along the shaft 18 at the proximal end of the balloon 101 along the shaft 18 of FIG. 1 would appear identical to that of FIG. 3.

Still referring to FIG. 3, the shaft 18 may have a guidewire lumen 81 and an inflation lumen 69. Typically, the guidewire lumen 81 extends longitudinally through the shaft 18 to the distal end of the shaft 18. Thus, the guidewire lumen 81 may be used to thread the balloon catheter 101 through narrow, tortuous vessels in a manner well known to those of ordinary skill in the art. The inflation lumen 69 is in fluid communication with the interior region of the balloon 101. Thus, the balloon 101 may be inflated by supplying a pressurized fluid, such as saline, to an inflation port. Similarly, the balloon 101 may be deflated from the inflated state by applying a negative pressure to the inflation port, which draws the fluid out of the balloon 101.

Figure 4:
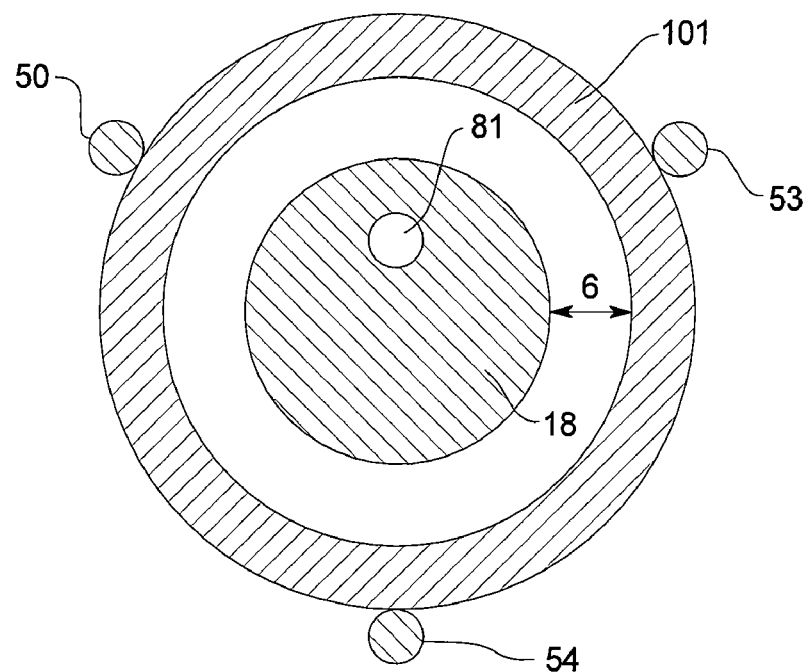
FIG. 4 is a cross-sectional end view of the balloon catheter along the working diameter and through the inflation lumen of the balloon shown in FIG. 1 with the balloon shown in an inflated state.

FIG. 4 is a cross-sectional view of the balloon catheter 100 along the working diameter and through the inflation lumen 69 of the balloon 101 shown in FIG. 1 with the balloon 101 shown in an inflated state. The dilation wires 50, 53, 54 are shown disposed adjacent to the outer surface of the balloon 101. The inflated balloon 101 creates a gap, G, between the outer surface of the catheter shaft 18 and the inner surface of the balloon 101.

Figure 5:
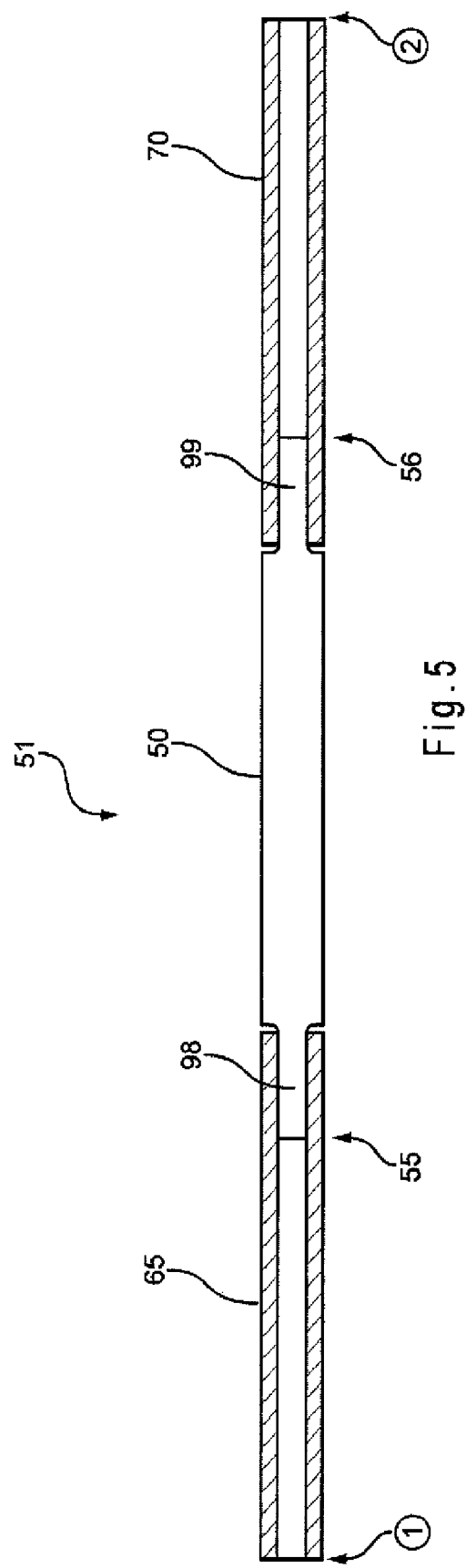
FIG. 5 shows one example of the attachment of the dilation wire to the coil.

The attachment of the dilation wire to the coil may be achieved in various ways. One example is illustrated in FIG. 5. FIG. 5 shows the dilation element 51 of FIG. 1 in which each of the ends 99 and 98 of the dilation wire 50 have been ground to a diameter that can fit within respective proximal coil 70 and distal coil 65. Other means for reducing the diameter of each of the ends of the dilation wire 50 are contemplated. The ground distal end 98 of the dilation wire 50 may be attached within distal coil 65 to create joint 55. Similarly, the ground proximal end 99 of the dilation wire 50 may be attached within proximal coil 70 to create joint 56. Each of the ends 98 and 99 of the dilation wire 50 is shown to extend a predetermined distance into their respective proximal and distal coils 70 and 65. The distance that each end of the wire 50 may extend into the proximal and distal coils 70 and 65 (i.e., the location of the joints 55 and 56) may be dependent upon the location at which the proximal and distal coils 70 and 65 are each affixed to the shaft 18. In particular, the location of joint 55 is at a different location from where the distal coil 65 attaches to the catheter shaft 18, and the location of joint 56 is at a different location from where the proximal coil 70 attaches to the catheter shaft 18. In the example of FIG. 5, the distal coil 65 may be affixed to the catheter shaft 18 at location "1" and the proximal coil 70 may be affixed to the catheter shaft 18 at location "2." The distance between joint 55 and location "1" represents the extent of stretchability that the distal coil 65 can provide as balloon inflates 101 and the dilation wire 50 dilates a stenosed region. Similarly, the distance between joint 56 and location "2" represents the extent of stretchability that the proximal coil 70 can provide as balloon 101 inflates and dilation wire 50 dilates the stenosed region. As shown in FIG. 5, the distance that each end of the wire 50 extends into proximal and distal coils 70 and 65 is shown to be substantially identical. Other distances may be contemplated and may be dependent upon locations "1" and "2." Each of the ends 98 and 99 of the dilation wire 50 may be attached to the inner surfaces of their respective coils 65 and 70 by any means known to one of ordinary skill in the art, including soldering or welding. Furthermore, although FIG. 5 shows the ground distal end and proximal end of dilation wire 50 affixed at a single coil element to create respective joints 55 and 56, the ground distal and proximal ends of the dilation wire 50 may be affixed to multiple coil elements. Additionally, the wire 50 may also be affixed to an outer surface of a coil. Numerous ways of affixing the wire to the coil are contemplated.

Figure 10:
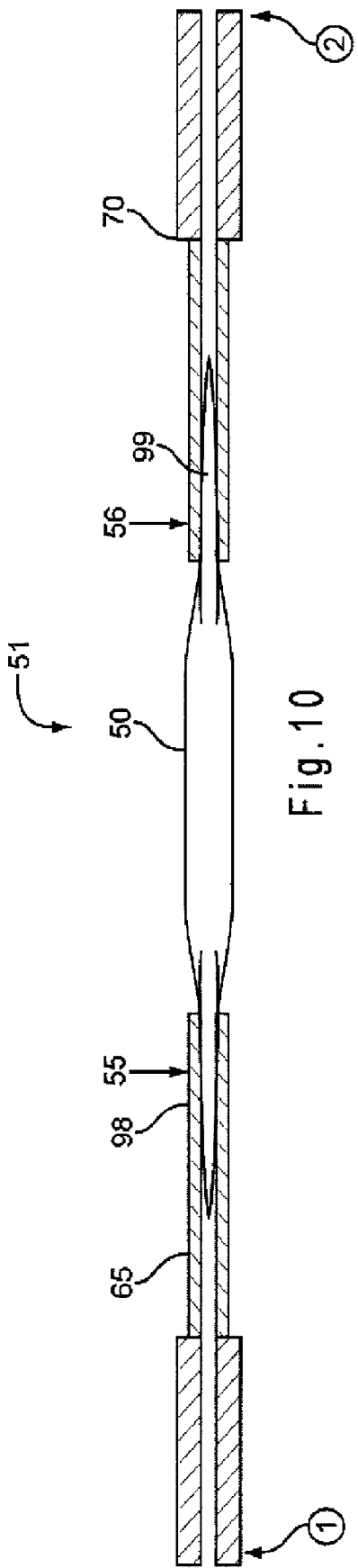
FIG. 10 is another example of how a dilation wire may be affixed to a coil.

FIG. 10 is another example of how a dilation wire may be affixed to a coil. FIG. 10 shows a dilation element 51 of FIG. 1 in which each of the ends 98 and 99 of the dilation wire 50 have been tapered to a diameter that can fit within respective proximal coil 70 and distal coil 65. Joint 55 may be created at a location where the tapered distal end 98 of dilation wire 50 contacts the inner surfaces of the distal coil 65. Similarly, joint 56 may be created at a location where the tapered proximal end 99 of dilation wire 50 contacts the inner surfaces of the proximal coil 70. Similar to the wire-coil configuration of FIG. 5, distal and proximal coils 65 and 70 may be affixed to the catheter shaft 18 at respective locations "1" and "2". A predetermined distance exists between location "1" and joint 55 and between location "2" and joint 56 to create sufficient stretchability of the coils 65 and 70 during inflation of the balloon 101. The stretchability of the coils 65 and 70 may enable the wire 50, which remains rigid, to dilate a stenosed region of a vessel without severing off from the surface of the balloon 101. Any length of taper of each of the ends 98 and 99 of the dilation wire 50 is contemplated. Although the dilation wire has been shown affixed to an inner surface of the coil, the dilation wire may be affixed to an outer surface of the coil. Additionally, numerous other ways of affixing the wire to the coil are contemplated.

As an alternative to each end of the dilation wire disposed within a proximal and distal coil, a single end of the dilation wire may be disposed within a single proximal or distal coil at one end of the balloon while the balance of the wire longitudinally extends along the entire balloon length and affixes directly to the shaft at the end of the balloon opposite to where the coil is disposed. The single proximal or distal coil extends from the working diameter of the balloon to the shaft where it is secured thereto. One end of the dilation wire may be affixed to the single coil in any number of ways, including those described above with respect to FIGS. 5 and 6.

Figure 11:
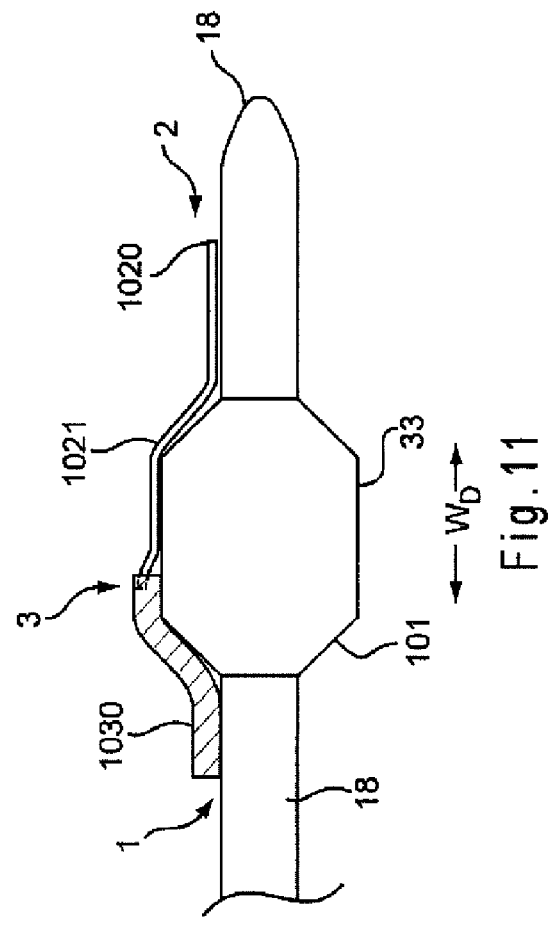
FIG. 11 is a side view of an alternative dilation wire-coil assembly in which a single end of the dilation wire is affixed to a proximal coil.

FIG. 11 shows an example of the above described single coil-dilation wire configuration. In particular, FIG. 11 shows the proximal end of dilation wire 1021 affixed to a single proximal coil 1030 at location "3". The proximal end of dilation wire 1021 may be affixed to the coil 1030 in numerous ways, including those described in FIGS. 5 and 10. The proximal coil 1030 extends proximally from the working diameter 33 of the balloon 101 to the shaft 18. The proximal coil 1030 may be affixed to the shaft 18 by an adhesive, such as glue, at location "1". The majority of the dilation wire 1021 may not be affixed to the coil 1030, as indicated in FIG. 11. Accordingly, the portion of the wire 1021 not affixed to the coil 1030 extends away from the coil 1030 in a distal direction. The wire 1021 distally extends along the working diameter 33, further extends down the tapered distal portion of the balloon 101, and terminates at the shaft 18. The distal end 1020 of the wire 1021 may be directly affixed to a surface of the shaft 18 at location "2", as shown in FIG. 11. The region along the proximal coil 1030 that is defined by the distance between locations "1" and "3" may provide the necessary stretchability of the coil 1030 to permit dilation wire 1021, which remains rigid, to dilate a stenosed region without severing from the outer surface of the balloon 101 as the balloon 101 expands. Although not shown, the single coil may be configured at the distal end of the balloon such that the coil extends distally from the working diameter of the balloon to the shaft. The dilation wire may be affixed to the distal coil and extend proximally along the working diameter, further extend down along the tapered proximal portion of the balloon, and terminate at the shaft where it may be directly affixed thereto.

Figure 8:
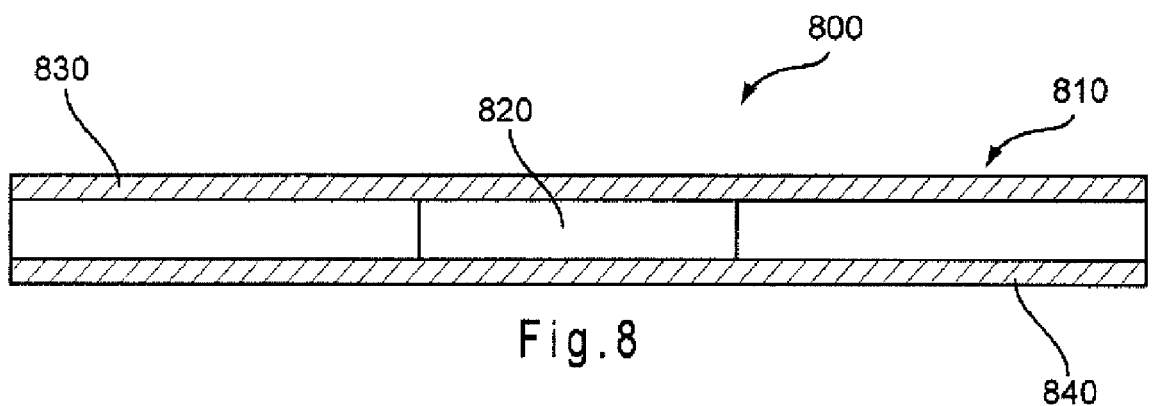
FIG. 8 illustrates a dilation wire-coil assembly in which a single coil extends the entire length of a balloon.

Other design configurations of dilation elements disposed along an outer surface of the balloon 101 may be utilized in addition to that of FIG. 1. FIG. 8 illustrates another dilation wire-coil assembly 800 in which a single coil 810 extends the entire length of a balloon. Each end of the coil 810 may be affixed by an adhesive to the shaft 18. A dilation wire 820 may have a length of about the length of a working diameter of the balloon and be inserted and affixed within the single coil 810. Dilation wire 820 is not shown to extend through distal coil 830 and proximal coil 840. The wire-coil assembly 800 may be positioned and affixed along a balloon 101 (FIG. 1) such that the dilation wire 820 extends substantially along the working diameter of the balloon 101 and the distal and proximal coils 830 and 840 extend from the working diameter 33 (FIG. 1) of the balloon 101 along distal and proximal tapered regions of the balloon 101 and terminate at the shaft 18, where they may be attached. The middle section of the coil 810 which has the wire 820 inserted therein remains rigid during inflation of the balloon 101, thereby enabling dilation of a stenosed region. Accordingly, coil regions 830 and 840 may provide the required stretchability during dilation.

Figure 6:
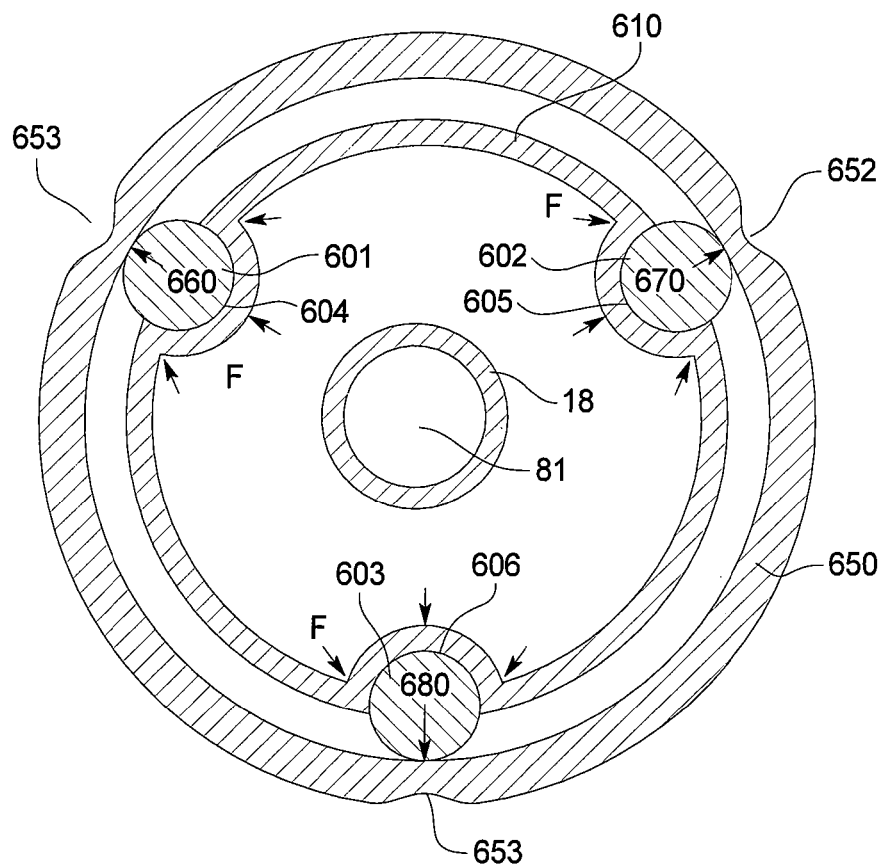
FIG. 6 is a partial cross-sectional view of a balloon catheter taken along a plane that is distal to the inflation lumen of a balloon that shows the forces exerted by the balloon against the dilation wires and thereafter transmitted to stenosed regions of a vessel wall.

The dilation mechanism will now be described. FIG. 6 is a partial cross-sectional view of a balloon catheter taken along a plane that is distal to the inflation lumen of a balloon 610. FIG. 6 shows the balloon 610 in an inflated state. Generally speaking, the dilation mechanism involves a technique in which the forces resulting from inflating an angioplasty balloon in a stenosis are concentrated and focused at one or more locations within the stenosis. While the technique has been shown to be useful in resolving resistant stenoses, it may also minimize the vascular trauma associated with balloon angioplasty and subsequently improve the outcome.

Referring to FIG. 6, the dilation wires 601, 602, 603 resist complete expansion of the balloon 610 at the balloon-dilation wire interfaces 604, 605, 606. As shown in FIG. 6, dilation wires 601, 602, 603 contact the stenosed regions 651, 652, 653 of the vessel wall 650. The interfaces 604, 605, 606 are shown as recessed due to the resistance of the dilation wires 601, 602, 603 against the surface of the inflated balloon 610. The dilation wires 601, 602, 603 may help to concentrate the force that the balloon 610 exerts upon inflation.

The balloon 610 will radially expand to the circumference shown in FIG. 6. The inflation pressure causes the balloon 610 to exert a force against each of the dilation wires 601, 602, 603. The force distribution is illustrated by a series of arrows which are designated F in FIG. 6. The force F is transmitted through each of three dilation wires 601, 602, and 603. This causes the dilation wires 601, 602, 603 to become pushed out toward the stenosed regions of the vessel wall 650.

As the force F is transmitted through each of the dilation wires 601, 602, 603, the dilation wires 601, 602, 603 focus the force, F, of the balloon 610 at the respective points of contact with the vessel wall 650, as shown by arrows 660, 670, and 680 of FIG. 6. Additionally, the dilation wires 601, 602, 603 may distribute the force longitudinally along the length of the balloon 610. This force concentration allows the dilation wires 601, 602, 603 to exert a higher stress at their respective points of contact with the stenosed regions 651, 652, 653 of the vessel wall 650 compared to conventional angioplasty balloons.

The force concentration feature enables dilation of the blood vessel 650 and/or cracking of the calcification rings contained in the blood vessel 650 at a relatively lower inflation pressure as compared to conventional angioplasty balloons. For example, the balloon catheter 101 of FIG. 1 is adapted to burst a calcification ring surrounding a blood vessel at an inflation pressure ranging between about 4 atm to about 9 atm. The exact inflation pressure is dependent upon numerous factors, including the diameter and geometry of the dilation wires used. Conventional angioplasty balloons may utilize inflation pressures of about 14 atm to about 15 atm. A lower inflation pressure is advantageous because it reduces the trauma to the vessel wall 650.

Additionally, the stress exerted by the dilation wires 601, 602, 603 is predictable and controlled, often requiring a single inflation. Because the dilations are predictable, controlled and often isolated to the stenosed segment of the vessel wall 650, restenosis may be limited to occurring only at the points of contact where the dilation wires 601, 602, 603 exert a stress at their respective points of contact 611, 612, 613 with the vessel wall 650. Conventional percutaneous transluminal coronary angioplasty (PTCA) procedures typically involve unpredictable points of rupture along the entire circumference of the blood vessel, which often results in more substantial vessel damage to the entire wall. Additionally, multiple inflations may be required to fracture a calcification ring.

The highest degree of cellular proliferation following balloon angioplasty typically occurs in areas with the greatest degree of vessel disruption. Therefore, the ability to dilate a stenotic region in a more controlled and less disruptive manner at a lower pressure, as described with respect to FIG. 6, may potentially minimize the degree of restenosis. Compared to PTCA procedures, the dilation wires 601, 602, 603 may be capable of providing a controlled dilatation in which the injury to the vessel wall is localized to the dilation site only. The balloon catheter 101 may require relatively lower inflation pressures and a relatively smaller number of inflations to produce significant increases in luminal cross section.

The optimal number of dilation wires may vary depending on the severity and type of stenosis to be dilated. Preferably, the number of wires will be at least two and the wires will be equidistant from each other.

Figure 9A:
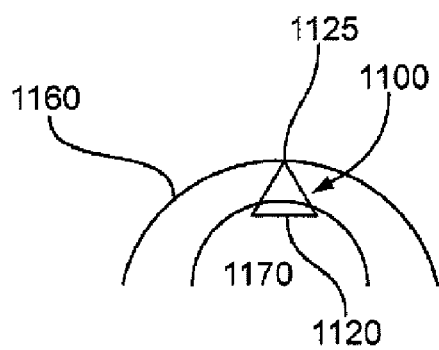
FIGS. 9a and 9b show a cross-sectional view of a circular-shaped wire pushed against a vessel wall and a polygonal-shaped wire pushed against a vessel wall.
Figure 9B:
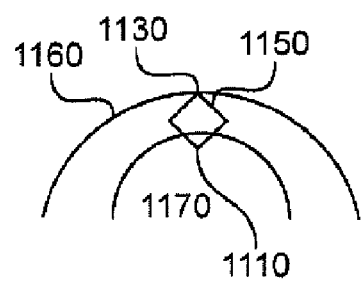

Various shapes of the wires may be used. Differing wire shapes enable the force that is concentrated on the vessel wall to be varied as desired. For instance, as shown in FIG. 9a, a polygonal-shaped cross-sectional wire 1100 may in certain applications be preferable over a circular-shaped cross-sectional wire 1150, as shown in FIG. 11b. The polygonal-shaped cross-sectional wire 1100 may increase the area of the wire 1120 in contact with the balloon 1170, relative to the area of the circular-shaped wire 1110 in contact with the balloon 1170 and minimize the area 1125 that contacts the vessel 1160, relative to the area of the circular-shaped wire 1130 in contact with the vessel 1160 (FIG. 9b). Accordingly, a higher stress may be exerted against the vessel wall 1160 by the polygonal-shaped wire 1100 relative to the circular-shaped wire 1150. Other non-circular shaped dilation wires may be used.

Although longitudinally extending dilation wires have been described, the dilation wires may also be formed to have other shapes in their relaxed state. For example, the dilation wires may be helixes that wrap around the balloon. Other shapes are also possible. Such configurations of the wires may be preferable for the purpose of minimizing the profile of the balloon catheter 101 during delivery to a target site as well as fracturing plaques having a tortuous geometry around a blood vessel.

If a substantially round cross-sectional configuration for the dilation wires is used, the diameters may vary depending on the particular blood vessel in which the stenosis is found and the size of the remaining lumen within the blood vessel. For round wires, a diameter of about 0.009 inches to about 0.17 inches is preferred. More preferably, the diameter may range from about 0.011 inches to about 0.15 inches.

Figure 7:
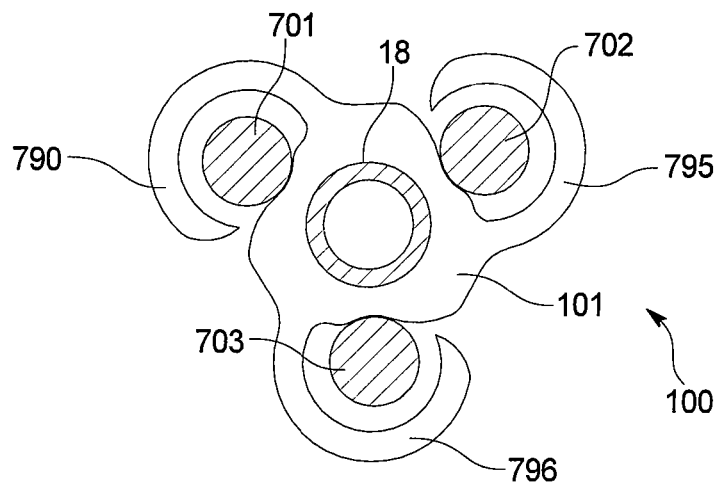
FIG. 7 is a partial cross-sectional view of a balloon catheter showing the balloon in a deflated state with the dilation wires wrapped into the flaps of the balloon.

FIG. 7 is a partial cross-sectional view of the balloon catheter 100 showing the balloon 101 in a deflated state with the dilation wires wrapped into the flaps 790, 795, 796 of the balloon 101. When the balloon 710 is deflated, the surface of the balloon 101 contains a plurality of creases that form flaps 790, 795, 796. The flaps 790, 795, 796 may fold around each of their respective dilation wires 701, 702, 703. The balloon catheter 100 is in such a folded, deflated configuration prior to insertion into a blood vessel. The folded configuration minimizes the profile of the balloon 101 during delivery. Although the flaps 790, 795, 796 are shown to extend partially around the dilation wires 701, 702, 703, the flaps 790, 795, 796 may completely wrap around the dilation wires 701, 702, 703 to shield the lumen of an artery from contact with the dilation wires 701, 702, 703 during delivery.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A balloon catheter for dilation of a vessel wall, comprising:
    a shaft having a distal end and a proximal end;
    a balloon mounted on the distal end of the shaft, the balloon having a distal portion, a proximal portion, wherein at least a length of an outer surface of the balloon comprises a working diameter adapted to dilate the vessel wall, the shaft having an inflation lumen extending therethrough in fluid communication with an interior region of the balloon, the balloon thereby being expandable between a deflated state and an inflated state; and
    a plurality of separate dilation elements each comprising a proximal coil, a distal coil, and a single dilation wire, the dilation wire having a proximal end, a distal end, and a middle portion, the middle portion of the dilation wire extending along the working diameter on the outer surface of the balloon, the proximal end of the dilation wire affixed to the proximal coil at a proximal joint where a diameter of the proximal end extends a predetermined distance into the proximal coil, wherein the proximal coil proximally extends from the working diameter of the balloon to the shaft, the distal end of the dilation wire affixed to the distal coil at a distal joint where a diameter of the distal end extends a predetermined distance into the distal coil, wherein the distal coil distally extends from the working diameter of the balloon to the shaft, the proximal and the distal coils being affixed to the shaft.

2. The balloon catheter according to claim 1, further comprising three of the dilation elements.

3. The balloon catheter according to claim 2, wherein each of the three dilation elements are circumferentially spaced about the outer surface of the balloon.

4. The balloon catheter according to claim 1, wherein the proximal end of each of the dilation wires is affixed to the proximal coil at a location different from the location where the proximal coil is affixed to the shaft.

5. The balloon catheter according to claim 1, wherein the distal end of each of the dilation wires is affixed to the distal coil at a location different from the location where the distal coil is affixed to the shaft.

6. The balloon catheter according to claim 1, wherein the middle portion of each of the dilation wires is rigid.

7. The balloon catheter according to claim 1, wherein the distal end of each of the dilation wires is affixed to the distal coil at a first location and the distal coil is affixed to the shaft at a second location, the distance between the first location and the second location defining a region of stretchability of the distal coil.

8. The balloon catheter according to claim 1, wherein the proximal end of each of the dilation wires is affixed to the proximal coil at a first location and the proximal coil is affixed to the shaft at a second location, the distance between the first location and the second location defining a region of stretchability of the proximal coil.

9. The balloon catheter according to claim 1, wherein the proximal end of each of the dilation wires and the distal end of each of the dilation wires are tapered.

10. The balloon catheter according to claim 1, the plurality of dilation elements are circumferentially disposed relative to each other, and wherein the balloon has a plurality of creases about the outer surface of the balloon, the plurality of creases forming flaps when the balloon is in the deflated state, the flaps folding around each of the plurality of dilation wires, the flaps being in substantial parallel alignment with the longitudinal axis of the balloon.

11. The balloon catheter according to claim 1, the proximal end of each of the dilation wires being affixed to the proximal coil at a location different from the location where the proximal coil is affixed to the shaft, the distal end of each of the dilation wires being affixed to the distal coil at a location different from the location where the distal coil is affixed to the shaft, the middle portion of each of the dilation wires being rigid, the distal end of each of the dilation wires being affixed to the distal coil at a first location and the distal coil being affixed to the shaft at a second location, the distance between the first location and the second location defining a region of stretchability of the distal coil, the proximal end of each of the dilation wires being affixed to the proximal coil at a third location and the proximal coil being affixed to the shaft at a fourth location, the distance between the third location and the fourth location defining a region of stretchability of the proximal coil, the plurality of dilation elements are circumferentially disposed relative to each other, and wherein the balloon has a plurality of creases about the outer surface of the balloon, the plurality of creases forming flaps when the balloon is in the deflated state, the flaps folding around each of the plurality of dilation wires, the flaps being in substantial parallel alignment with the longitudinal axis of the balloon, the proximal end of the dilation wires being affixed to the proximal coils and the distal end of the dilation wires being affixed to the distal coil.

* * * * *